United States Patent

Jaeggi

[11] Patent Number: 5,574,224
[45] Date of Patent: Nov. 12, 1996

[54] PROCESS AND DEVICE FOR THE CONTINUOUS NONDESTRUCTIVE CONTROL OF RAILS ON A RAILWAY LINE BY ULTRASONICS

[75] Inventor: Jean-Pierre Jaeggi, Geneva, Switzerland

[73] Assignee: Speno International S.A., Geneva, Switzerland

[21] Appl. No.: 459,627

[22] Filed: Jun. 2, 1995

Related U.S. Application Data

[63] Continuation of Ser. No. 162,705, Dec. 7, 1993, abandoned.

[30] Foreign Application Priority Data

Dec. 23, 1992 [CH] Switzerland .............................. 3928/92

[51] Int. Cl.$^6$ .................................................. G01N 29/04
[52] U.S. Cl. ............................................... 73/636; 73/634
[58] Field of Search ............................ 73/636, 634, 635, 73/620, 624, 625, 628, 641

[56] References Cited

U.S. PATENT DOCUMENTS

| | | | |
|---|---|---|---|
| 3,592,052 | 7/1971 | Di Giacomo et al. | 73/620 |
| 3,683,680 | 8/1972 | Johnson et al. | 73/636 |
| 4,004,455 | 1/1977 | McKee et al. | 73/636 |
| 4,235,112 | 11/1980 | Kaiser | 73/634 |
| 4,457,178 | 7/1984 | Turbe et al. | 73/636 |
| 4,487,071 | 12/1984 | Pargano et al. | 73/636 |
| 4,593,569 | 6/1986 | Joy | 73/636 |
| 4,689,995 | 9/1987 | Turbe | 73/634 |
| 4,700,574 | 10/1987 | Turbe | 73/636 |
| 5,275,051 | 1/1994 | De Beer | 73/634 |

FOREIGN PATENT DOCUMENTS

| | | |
|---|---|---|
| 2 244 173 | 4/1975 | France . |
| 672 958 | 1/1990 | Switzerland . |
| WO85/04485 | 10/1985 | WIPO . |

OTHER PUBLICATIONS

"Ultrasonic Flaw Evaluation in Rails With Assistance of Programmable Calculator"; Rogovsky, Alexander and Thomas, Jerrell; *Material Evaluation;* 1981.

*Primary Examiner*—Hezron E. Williams
*Assistant Examiner*—Helen C. Kwok
*Attorney, Agent, or Firm*—Young & Thompson

[57] ABSTRACT

A continuous nondestructive process for controlling the rails on a railway line by ultrasounds is carried out by the emission of ultrasounds at successively different points along the rail which are spaced apart by a measured value. For each echo, the acoustic distance between the point of emission and the point of reflection of the beam of ultrasounds is determined, and then a bidirectional map of the echoes is established by correlation. Finally, this echo map is compared to a mask having a window, of which the shape, the orientation and the dimensions are determined by the characteristic features of the rail to be examined and by the type of defect looked for, only those echoes which appear in this window being then taken into consideration.

13 Claims, 2 Drawing Sheets

1

PROCESS AND DEVICE FOR THE CONTINUOUS NONDESTRUCTIVE CONTROL OF RAILS ON A RAILWAY LINE BY ULTRASONICS

This application is a continuation of application Ser. No. 08/162,705, filed Dec. 7, 1993, now abandoned.

BACKGROUND OF THE INVENTION

1. Field of the Invention

The present invention relates to a process and a device for the continuous nondestructive control of rails on a railway line by ultrasonics.

2. Description of the Related Art

Devices for continuously controlling rails on a railway line by ultrasonics are described for example in the documents WO/8504485 or U.S. Pat. No. 4,235,112 and they include generally ultrasound emitting—receiving probes in acoustic contact with the upper rail surface as well as an electric device for processing the signals generated by the echoes of the ultrasounds emitted.

One of the major difficulties when controlling rails on a railway line by ultrasonics arises from the need to discriminate between the acoustic reflections or echoes produced by the rail defects which are to be located and identified, and those either generated by specific and normal features of the rail, such as the fishplate holes, the ends of rails, etc, or arising from interferences of an electric or an acoustic nature.

On existing machines, this discrimination can be achieved in two ways:

The signals produced by the ultrasonic probes are displayed, and more generally printed on the chart paper of an all or nothing multitrack reorder, in which the progression of the paper can be controlled by the forward motion of the machine. It is up to the operator to decide from the recording whether a defect was detected or not. This operation can be carried out either in real time by the permanent observation of the recording, or later in the laboratory.

Additional logic inhibition circuits are added to the control system, which are based on the principle that consecutive pulses are counted at given acoustic distances corresponding to the areas in which certain known particular features of the rail can be anticipated.

These methods suffer however the following drawbacks:

The first method, based on human judgement, is highly dependent upon the experience and the reliability of the operator, and the results can therefore be highly variable.

The second method is less influenced by personal judgment and is more reliable, but the logic levels are most of the time restricted to simple counts and, therefore, lack flexibility because the algorithms are defined by construction and allow no adaptation in real time by the operator according to the conditions of the rail being controlled. Further, they cannot eliminate completely interfering echoes or signals.

Further documents are known, i.e. U.S. Pat. No. 3,592,052 and FR 2,244,173, which describe installations for the control of manufactured parts by ultrasonics. These installations are not designed for the control of rails on a railway line, but for the factory control of machined parts or of metal sheets. These installations cannot be adapted to in situ inspections and hence differ fundamentally from our invention.

U.S. Pat. No. 3,592,052 describes an ultrasonic probe which is moved along the part to be controlled and in which the positions of the probe where a maximum echo or no echo is found are identified and measured. This information is then used for calculating the depth of the defect.

French patent 2 244 173 describes the displacement above a part to be controlled of an ultrasonic device designed for identifying areas where the echoes are intercepted by defects. The use of several groups of sensors with different orientations ensures that no defect is overlooked in the control.

None of these installations either are capable of excluding interfering signals and they suffer therefore from the same drawbacks as those mentioned above.

SUMMARY OF THE INVENTION

To analyze the acoustic signals, the invention relies on a system, which is of a more sophisticated nature.

The process and the device according to the invention are designed for discriminating between signals or selecting automatically the signals or the echoes corresponding to defects of the rail, while eliminating those signals either due to the normal characteristics of the rail or to interferences. Further, the present invention also makes it possible to categorize or classify the defects found in the rails according to their type.

The process and the device according to the invention are defined in the independent claims of the present patent.

BRIEF DESCRIPTION OF THE DRAWINGS

The appended drawing illustrates schematically and by way of example an embodiment of the device for implementing the process of the invention.

DESCRIPTION OF THE PREFERRED EMBODIMENTS

Figure 1:
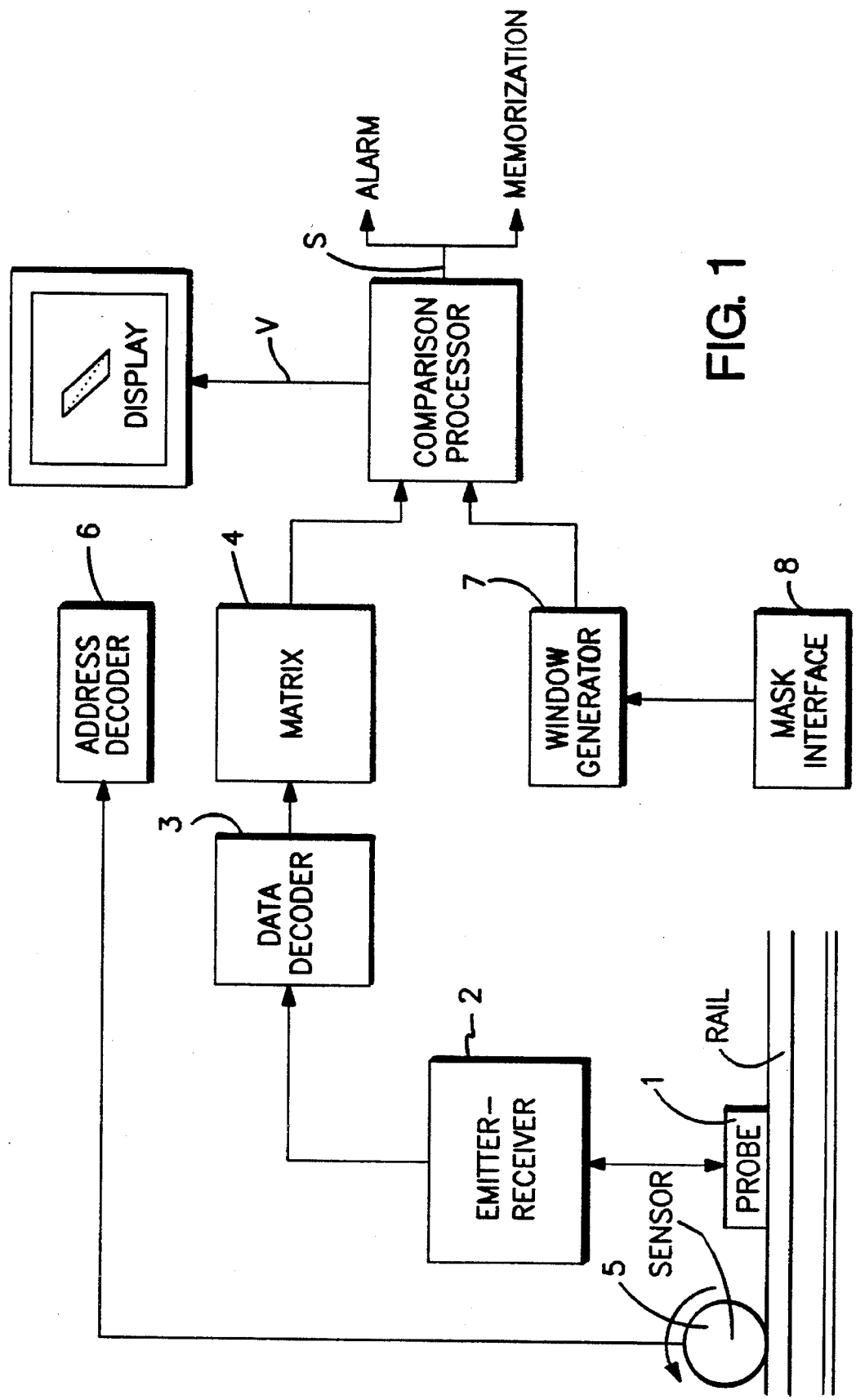
FIG. 1 is a block diagram of the control device.

The present process and the device for carrying out the same are based on the fact that the defects in the rail are not of a random nature but exhibit characteristic features which are known and constant, and which depend upon their type (orientation, position, environment).

Each type of defect has therefore an "acoustic signature" which is characteristic thereof and which distinguishes it from other features which may give rise to acoustic responses.

In its principle, the process upon which the device is based, hence consists in memorizing the successive acoustic responses as the ultrasonic probe travels past the defect.

The content of this memory is displayed as a map representation or as a matrix, in which the X-axis represents the stepwise progression of the probe and the Y-axis the acoustic distance of the first reflection on the heterogeneity of the rail.

Upon the first detection, a mask or a filter of a variable shape is positioned automatically on the matrix, thus defining a zone in which the following detections are to appear.

Any appearance outside this mask is not taken into account, which thus eliminates any information not related to the defect considered (interference signals, other anomalies, etc).

The responses which conform to the mask set off an alarm and/or are memorized for later processing.

Each matrix and its associated mask are displayed on a screen and the operator can, at any moment, modify the parameters of the mask (angle, number of steps in the X-direction, number of steps in the Y-direction, number of consecutive steps, etc) for adaptation to the conditions of the rail to be controlled.

The advantages of this device are of two orders:

A better discrimination of the defects is made possible through the elimination of any information which does not correspond to the signature of the type of defect looked for.

The equipment is simpler to use because of the visual display of the matrices and of the masks, and because the shape of the masks can be easily modified in real time by the operator.

In the continuous and nondestructive control process for a rail on a railway line according to the present invention, a beam of ultrasounds is sent into the rail and the reflected echoes are recorded, to be subsequently transformed into electric signals which represent the distance of the detected defect from the probe.

Simultaneously, the position or the progression of the probe along the rail is measured, and by combining the signals representing the distance of the defect from the probe and the position of the probe along the rail, a map representation of the echoes received is selected.

At the same time, the operator chooses a mask or an electric window and superposes the same upon the map representation of the echoes. This enables a selection of the echoes restricted to only those which fall inside the window of the mask and correspond therefore to the signature of a defect looked for. An alarm is set off automatically, when a given ratio of echoes falling inside the window of the mask is reached. Obviously, one can also display and/or memorize the result of the comparison or superposition of the mask and of the map representation of the echoes. It is clear that the shape of the window of the mask, its dimensions, its length, width and slope can be selected according to the type of defect looked for and according to the characteristic features of the rail being examined.

This process makes it possible to detect automatically the defects of a rail, without the need to recourse to human judgment, while at the same time having the freedom to modulate the result of the measure according to the defects looked for and the characteristic features of the rail being examined. It is therefore possible to combine flexibility and facility of control.

Figure 2:
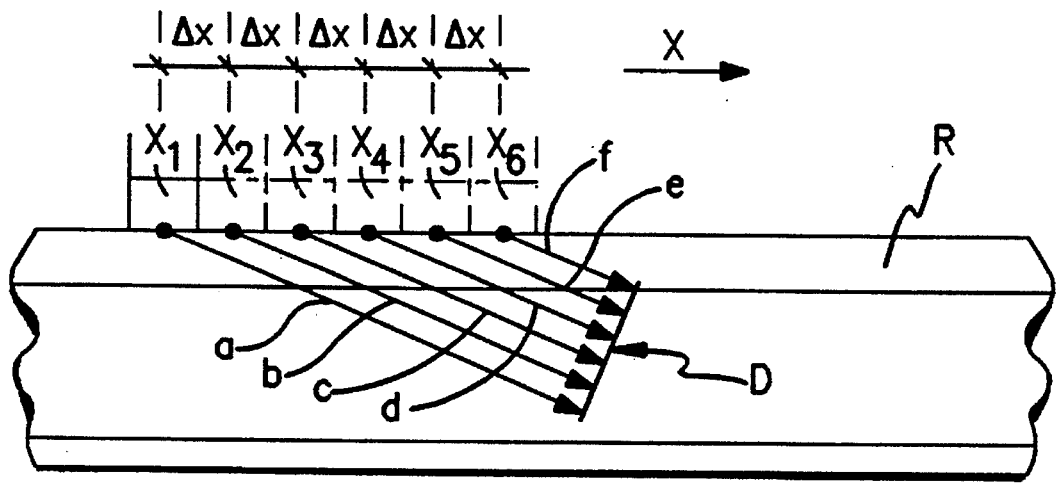
FIG. 2 illustrates different successive positions of the probe relatively to a defect of the rail.
Figure 3:
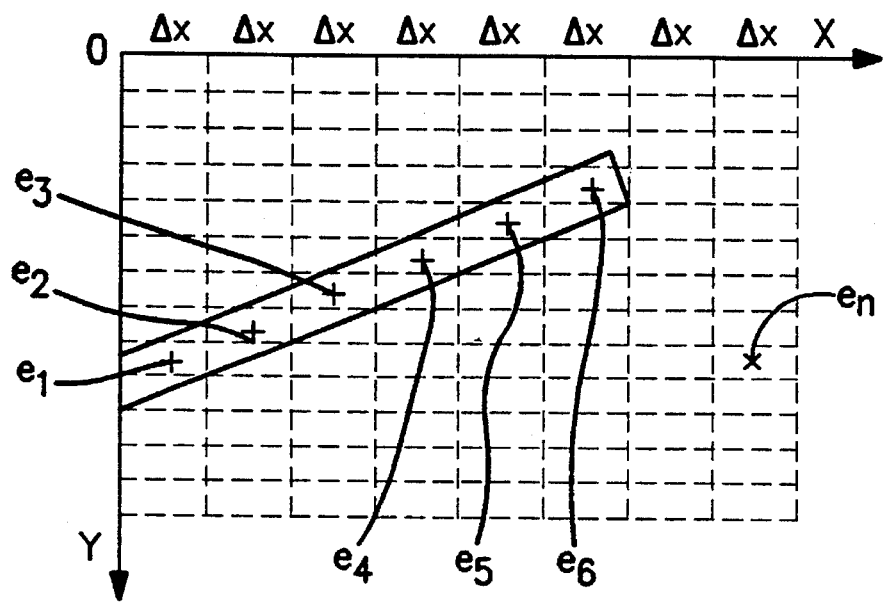
FIG. 3 illustrates the graphical representation of the defect detected in FIG. 2.

FIGS. 2 and 3 illustrate schematically the map representation of the echoes.

In FIG. 2, one can see the successive positions X1, X2, . . . X6 of the probe along the rail R spaced by intervals amounting to $\Delta x$, and the distance travelled a, b, c, . . . , f by a beam of ultrasounds between said probe and a defect D.

In FIG. 3, one can see the map or matrix representation X, Y of the echos E1, E2, . . . E6 of a defect D, as a function of the position of the probe along the rail.

In the example illustrated, the echoes E1–E6 are aligned along a straight line and correspond therefore to the defect illustrated in FIG. 2. An echo En is immediately recognized as being non-coherent and therefore to be eliminated.

The device for carrying out the control process described is illustrated schematically in FIG. 1. It includes an ultrasonic probe 1 which is in acoustic contact with a rail R to be examined and which can move along this rail. This probe 1 is connected to an ultrasound emitter-receiver 2. The ultrasound receiver delivers electric signals corresponding to the echoes received to a data decoder 3, which supplies the map memories or matrix 4 with signals representing the distance or the travel time of the ultrasounds between the probe and a defect detected in the rail. This device further includes a sensor 5 supplying signals representing the displacements of probe 1 with respect to rail R, to an address decoder 6 connected to matrix 4. A map representation of the echoes received is thus generated in matrix 4, as is illustrated in FIG. 3.

The control device further includes a mask or window generator 7 controlled manually by the operator via an interface for adjusting the parameters of masks 8, and the signals representing selected masks, also forming a X,Y-matrix, are fed to a comparator 9, which also receives the signals representing the matrix of the map memory 4.

This comparator delivers to a display screen signals V corresponding to a video representation of the superposition of the mask and of the map memory of the echoes, as well as an output signal S for setting off an alarm and/or for memorizing the results of the comparison carried out.

Should several different types of defects be looked for, one can obviously compare the content of the matrix or of the map memories 4 simultaneously or successively with several different masks.

This process and this device make it possible to eliminate completely the echoes or interferences, and also any anomaly of the rail, when its signature does not correspond to the defect looked for, is eliminated completely and automatically.

Modifications of the invention herein disclosed will occur to a person skilled in the art and all such modifications are deemed to be within the scope of this invention as defined by the appended claims.

I claim:

1. A continuous nondestructive control process for rails on a railway line comprising the steps of:

moving a probe along and in acoustic contact with a rail of said railway line;

successively emitting beams of ultrasounds into a rail head at different points along the rail spaced by a measured distance;

receiving ultrasound echoes of said successive beams of ultrasounds reflected from obstacles situated inside said rail;

measuring, for each of said ultrasound beams emitted into said rail head, and acoustic distance between each of said different points along the rail and points at which said obstacles inside said rail generate a reflection of said emitted ultrasound beams;

establishing a bidirectional map of said received ultrasound echoes by correlating a distance between each of said different points with said acoustic distance for each of said received ultrasound echoes;

performing a comparison and a superposition of said bidirectional map with at least one selected mask having a window, of which a shape, orientation, and dimensions are determined by characteristic features of said rail and by a type of obstacle to be located, thereby allowing an identification of the type and shape of obstacles situated inside said rail.

2. A process according to claim 1, wherein said bidirectional map is compared with a plurality of mutually different masks corresponding to different types of obstacles.

3. A process according to claim 1, wherein said superposition of said bidirectional map on said at least one mask is displayed visually on a display means.

4. A process according to claim 2, wherein said bidirectional map is simultaneously compared to each of said plurality of masks.

5. A process according to claim 2, wherein said bidirectional map is sequentially compared to each of said plurality of masks.

6. A process according to claim 1, wherein said bidirectional map is superimposed on a plurality of mutually different masks corresponding to different types of obstacles.

7. A process according to claim 6, wherein said bidirectional map is simultaneously superimposed on each of said plurality of masks.

8. A process according to claim 6, wherein said bidirectional map is sequentially superimposed on each of said plurality of masks.

9. A process according to claim 1, wherein said window of said mask is created upon reception and mapping of at least a first ultrasound echo of said received ultrasound echoes reflected from said obstacles situated inside said rail, said window thus delimiting a zone in which subsequent ultrasound echoes are to appear.

10. A process according to claim 9, wherein when at least one ultrasound echo of said received ultrasound echoes is received that fits within the window of the mask, an acoustical signature of said at least one ultrasound echo triggers at least one of a memorization of said acoustical signature and an alarm.

11. A process according to claim 8, wherein said obstacles inside said rails are defects within said rail.

12. A device for continuous nondestructive control of rails on a railway comprising:

a probe mobile along a rail and in acoustic contact with said rail;

an ultrasound emitter-receiver coupled with said probe emitting ultrasound beams and receiving ultrasound echoes reflected back to said emitter-receiver by obstacles situated inside said rail;

a device for measuring a displacement of said probe along said rail;

an echo map memory means for receiving signals from an address decoder supplied by said device for measuring the displacement of the probe along the rail and from a data recorder supplied by said ultrasound emitter-receiver, said echo map memory means establishing a bidirectional echo map of said ultrasound echoes received by said ultrasound emitter-receiver;

a comparator processor receiving output signals from said echo map memory means and from a mask generator, said comparator processor comprising means for delivering, to a display screen, signals corresponding to a video representation of a superposition of said bidirectional echo map with at least one selected mask generated by said mask generator and further comprising means for generating a signal for triggering an alarm and a signal for memorizing results of a comparison carried out by said comparator processor, each of said at least one selected mask corresponding to a different type of obstacle to be located inside said rail.

13. A device according to claim 12, wherein said mask generator is controlled via an adjusting means for adjusting at least one of a shape, orientation and dimensions parameters of said mask.

* * * * *